United States Patent [19] [11] 4,061,640
Cavalla et al. [45] Dec. 6, 1977

[54] 2-(BENZAMIDO PIPERIDINE) QUINOLYL DERIVATIVES

[75] Inventors: John Frederick Cavalla, Isleworth; John Leheup Archibald, Windsor, both of England

[73] Assignee: John Wyeth & Brother Limited, Maidenhead, England

[21] Appl. No.: 709,671

[22] Filed: July 29, 1976

Related U.S. Application Data

[63] Continuation-in-part of Ser. No. 524,029, Nov. 15, 1974, abandoned, which is a continuation-in-part of Ser. No. 323,684, Jan. 15, 1973, abandoned, and a continuation-in-part of Ser. No. 175,345, Aug. 26, 1971, abandoned.

[30] Foreign Application Priority Data

Sept. 3, 1970 United Kingdom ............... 42090/70
July 22, 1971 United Kingdom ............... 34376/71

[51] Int. Cl.² .......................................... C07D 215/14
[52] U.S. Cl. .............................. 260/287 CE; 424/258
[58] Field of Search ..................... 260/287 CE, 287 R

[56] References Cited

U.S. PATENT DOCUMENTS 3,813,398 5/1974 Aumüller et al. ............. 260/283 SA
3,991,062 11/1976 Idel et al. ...................... 260/287 CE
3,992,386 11/1976 Schacht et al. ................ 260/287 CE
4,029,801 6/1977 Cavalla et al. ........................ 424/267

Primary Examiner—Donald G. Daus
Assistant Examiner—David E. Wheeler
Attorney, Agent, or Firm—Arthur E. Wilfond

[57] ABSTRACT

Compounds of the formula

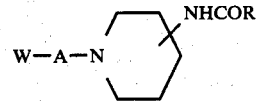

in which
W is quinolyl or lower alkyl quinolyl;
A is alkylene of 1 to 6 carbon atoms;
R is phenyl, halophenyl, lower alkoxy phenyl or lower alkyl phenyl;
or a pharmaceutically acceptable acid addition salt thereof, are hypotensive and bradycardial agents.

5 Claims, No Drawings

2-(BENZAMIDO PIPERIDINE) QUINOLYL DERIVATIVES

RELATED APPLICATIONS

This application is a continuation-in-part of copending application Ser. No. 524,029, filed Nov. 15, 1974, now abandoned which is a continuation-in-part of application Ser. No. 323,684, filed Jan. 15, 1973, now abandoned, which in turn was a continuation-in-part of application Ser. No. 175,345 filed Aug. 26, 1971, now abandoned.

DESCRIPTION OF THE INVENTION

In accordance with this invention, there is provided a group of compounds of the formula

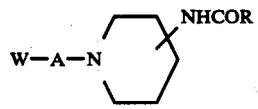

in which
  W is quinolyl or lower alkyl quinolyl;
  A is alkylene of 1 to 6 carbon atoms;
  R is phenyl, halophenyl, lower alkoxy phenyl or lower alkyl phenyl;
or a pharmaceutically acceptable acid addition salt thereof. These compounds are hypotensive agents and bradycardial agents in that they lower blood pressure and reduce the rate of heart beat in warm blooded animals.

The compounds of this invention preferably contain the —NHCOR group in 4-position of the piperidine ring. Most preferably the R group is phenyl, the optional halo-, lower alkoxy- and lower alkyl- substituents being functionally equivalent variations of the unsubstituted phenyl ring. Likewise, the presence of a lower alkyl substituent in the quinolyl moiety does not materially alter the activity spectrum of the compounds of the invention. Of the quinolyl group embraced by the invention, the 2-quinolyl group is preferred from the standpoint of its ready availability and production economics. The alkylene group represented by A can be either branched or straight chain, the latter being preferred. Chlorine, bromine and fluorine represent preferred halogens and the lower alkyl, lower alkylene, or lower alkoxy groups preferably contain from one to four carbon atoms, although from 1 to 6 carbon atoms are appropriate functional equivalents.

The acid addition salts are formed by reaction of the depicted bases with a pharmaceutically acceptable organic or inorganic acid such as sulfuric, hydrochloric, hydrobromic, hydroiodic, nitric, phosphoric, methane sulfonic, p-toluene sulfonic, acetic, maleic, fumaric, tartaric, formic acid, and the like.

The compounds of this invention can be prepared in a number of ways by building up the molecule from suitable starting materials in known manner.

One method of preparation comprises reacting an acylaminopiperidine of the general formula

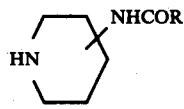

with an alkylating or acylating agent of the general formula

[W]—A—Y where R, W, and A have the meanings already defined and Y is a halogen atom or an equivalent replaceable atom or radical, for example an organic sulfonyl radical such as tosyl radical. Alternatively, a vinyl substituted compound of formula

[W]—B wherein B is a straight or branched chain alkenyl radical, preferably a vinyl radical may be reacted with the acylaminopiperidine to give the desired compounds wherein A is a straight or branched chain alkylene radical.

The reactants [W]—A—Y and [W]—B are known compounds or can be made following the methods known for preparing compounds of these types.

The acylaminopiperidine reactant is produced by acylating a corresponding amino compound of the general formula

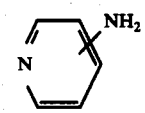

and reducing the ring system to the corresponding tetrahydropyridine or piperidine ring. The acylaminopiperidine reactant is preferably prepared by either (i) forming the oxime or an N-benzyl-4-piperidone, reducing to give the 4-amino compound, acylating the amino group and then hydrogenolyzing the benzyl residue, or (ii) treating the pyridine of formula

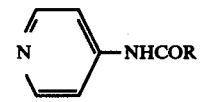

with a benzyl halide, for example benzyl chloride to give the quaternary salt, reducing with an alkali metal borohydride to give the corresponding N-benzyl-tetrahydro-pyridine which is further subjected to concomitant de-benzylation and reduction of the 3,4-double bond by catalytic hydrogenation, or (iii) catalytic hydrogenation of the above acylaminopyridine compound in the presence of acetic anhydride to give

and then selectively hydrolyzing the acetyl group.

A still further aspect of the invention is the provision of a further process for preparation of compounds of the invention which consists of reacting a compound of the general formula

[W]—A—OH (in which W, and A have the meanings defined above) with the acylaminopiperidine reactant. The reaction is preferably carried out in the presence of a catalyst, for example Raney Nickel. An organic solvent, which is inert under the reaction conditions, is usually used, for example xylene, toluene, or benzene. Preferably the reaction is carried out by heating the reactants under reflux in a water-immiscible organic solvent, for example xylene, and removing the water formed during the reaction by azeotropic distillation. If necessary, reactive substituent groups can be blocked during a reaction and released later.

The reactions outlined above usually are carried out in a solvent which is inert under the reaction conditions. The most suitable solvent system is chosen and varies depending on the particular reactants being employed. If necessary heating the reactants in solution under reflux can be carried out, and if necessary heating under high pressures may also be used.

The acyl group —COR may be tailored as desired, by hydrolysis and reacylation with a different —COR group.

Compounds in which A is a branched chain alkylene radical possess an asymmetric carbon atom and are therefore capable of existing in optically active stereo isomeric forms. The optical isomers may be separated by standard resolution procedures. For instance the compounds contain basic nitrogen atoms and may generally be resolved by treatment with a suitable optically active acid. Optically active acids are described in the literature and suitable ones for the resolution of any particular compound are chosen by experiment.

If necessary, in any of the reactions hereinbefore described, reactive substituent groups may be blocked during a reaction and released at a later stage. As already indicated the novel piperidine compounds provided by the invention contain a basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

The compounds of this invention, optionally in micronized form may be formulated into pharmaceutical compositions, containing a non-toxic carrier. Any suitable carrier known in the art can be used to prepare the pharmaceutical compositions. In such a composition, the carrier may be a solid, liquid, or a mixture of a solid and a liquid. Solid form compositions include powders, tablets and capsules. A solid carrier can be one or more substances which may also act as flavoring agents, lubricants, solubilizers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection. Either solid or liquid compositions may be administered orally.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following non-limiting Examples illustrate the preparation of the compounds of the invention:

EXAMPLE 1

1-[2-(2-Quinolyl)ethyl]-4-benzamidopiperidine 2-(2-Hydroxyethyl)quinoline (5.0 g.) in thionyl chloride (15 ml.) was heated at 50° C. for 30 minutes. Excess thionyl chloride was removed and the residue was added to 4-benzamidopiperidine (4.74 g.) and potassium carbonate (12.0 g.) in dimethylformamide (25 ml.). The reaction mixture was stirred under reflux for 18 hours, cooled and shaken with water and ether. The ether extracts were dried and evaporated and the residue in acetonitrile was acidified with dry hydrogen chloride to give the product as the dihydrochloride, m.p. 198° C. (dec.). (Found: C, 63.7; H, 6.3; N, 9.7. $C_{23}H_{25}N_3O.2HCl$ requires C, 63.9; H, 6.3; N, 9.7%).

EXAMPLE 2

The following compounds were prepared in a similar manner to that described in the hereinbefore disclosed Example 1-[4-(Quinol-2-yl)but-1-yl]-4-benzamidopiperidine;
1-[5-(Quinol-2-yl)pent-1-yl]-4-benzamidopiperidine;
1-[6-(Quinol-2-yl)hex-1-yl]-4-benzamidopiperidine;
1-[2(Quinol-2-yl)eth-1-yl]-4-benzamidopiperidine;

1-[3(Quinol-2-yl)prop-1-yl]-4-benzamidopiperidine; and
1-[4(Quinol-2-yl)but-1-yl]-4-benzamidopiperidine.

EXAMPLE 3

Following the procedure of Example 1 but replacing 4-benzamidopiperidine by the indicated alternative starting material the indicated end products can be prepared:

| benzamidopiperidine | end product |
| --- | --- |
| 4-(2-chloro)-benzamido-piperidine | 1-[2-(2-Quinolyl)-ethyl]-4-(2-chloro)-benzamidopiperidine |
| 4-(3-methoxy)-benzamido-piperidine | 1-[2-(2-Quinolyl)-ethyl]-4-(3-methoxy)-benzamidopiperidine |
| 4-(4-methyl)benzamido-piperidine | 1-[2-(2-Quinolyl)-ethyl]-4-(4-methyl)-benzamidopiperidine |

EXAMPLE 4

Following the procedure of Example 1 but replacing 2-(2-hydroxyethyl)quinoline by 2-(2-hydroxyethyl)-4-methylquinoline there can be prepared 1-[2-(2-(4-methylquinolyl)-ethyl]-4-benzamidopiperidine.

The hypotensive and bradycardial activity of 1-[2-(2-(4-methylquinolyl)ethyl]-4-benzamidopiperidine, which compound is representative of the entire group of compounds of the invention, was established by the following standard, science recognized testing procedure: Rats were anesthetized with pentobarbitone sodium (60 mg/kg) and the jugular vein, trachea and carotid artery were cannulated. The test compound was given intravenously at 15 min. intervals (dose range 0.8–25.6 mg/kg cumulative) and blood pressure and heart rate were recorded via the carotid artery at 30 second and 15 minutes after administration. The production of a fall of 30 mm. mercury in diastolic pressure from control values is considered to be significant while a fall of greater than 75 mm. mercury is considered to be marked hypotensive activity. A decrease in heart rate of more than 25 beats per minute from control values was considered to be significant while a drop of greater than 100 beats per minute is considered to be marked bradycardia.

The product of Example 1 consistently demonstrated, in repeated testing, blood pressure lowering activity in excess of about 36 mm. Hg., 15 minutes after administration of a dose of 25.60 milligrams per kilogram host body weight, with most replicate tests reflecting a drop of in excess of 70 mm. Hg, at that dosage. A heart rate beat reduction of about 25 beats per minute was consistently obtained with the compound of Example 1 at a dose of 12.80 milligrams per kilogram host body weight, with a most frequent reduction in excess of 100 beats per minute at a dose of 25.60 milligrams per minute.

Thus, the compounds of this invention, by analogy with the product of Example 1 are useful in the treatment of warm blooded animals requiring hypotensive or bradycardial modification of their cardiovascular system, which problems frequently occur with patients suffering from angina pectoris and various arrhythmic dysfunctions.

The product of Example 1 also possesses anti-histaminic activity as determined by the method of Alps et al., Br. J. Pharmacol., 1972, 44, 52-62, and is useful as an anti-allergic agent in control of those allergic responses characterized by histamine release, such as urticaria, pruritis, allergic rhinitis, anaphylactic shock and bronchial asthma.

We claim:

1. A compound of the formula

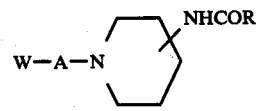

in which
W is 2-quinolyl or lower alkyl 2-quinolyl;
A is alkylene of 1 to 6 carbon atoms;
R is phenyl, halophenyl, lower alkoxy phenyl or lower alkyl phenyl;
or a pharmaceutically acceptable acid addition salt thereof.

2. A compound of claim 1 of the formula

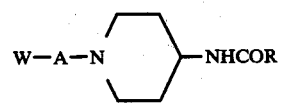

wherein
W is 2-quinolyl or lower alkyl 2-quinolyl;
A is alkylene of 1 to 6 carbon atoms;
R is phenyl, halophenyl, lower alkoxy phenyl or lower alkyl phenyl;
or a pharmaceutically acceptable acid addition salt thereof.

3. A compound of claim 1 of the formula

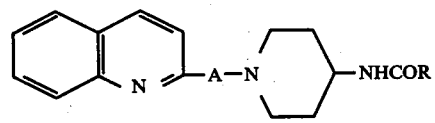

wherein
A is alkylene of 1 to 6 carbon atoms;
R is phenyl, halophenyl, lower alkoxy phenyl or lower alkyl phenyl;
or a pharmaceutically acceptable acid addition salt thereof.

4. A compound of claim 1 of the formula

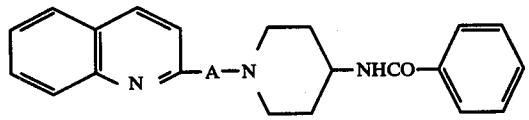

wherein A is alkylene of 1 to 6 carbon atoms or a pharmaceutically acceptable acid addition salt thereof.

5. A compound as claimed in claim 1, which is 1-[2-(2-quinolyl)ethyl]-4-benzamidopiperidine or a pharmaceutically acceptable acid addition salt thereof.

* * * * *